United States Patent [19]

Smoll

[11] Patent Number: 5,450,758
[45] Date of Patent: Sep. 19, 1995

[54] BIOPROBE REPLACEMENT SENSOR AND TRANSDUCER

[76] Inventor: Owen C. Smoll, 2260 Monaco Dr., Oxnard, Calif. 93035

[21] Appl. No.: 311,022

[22] Filed: Sep. 23, 1994

[51] Int. Cl.$^6$ .............................................. G01F 1/58
[52] U.S. Cl. .............................. 73/861.12; 73/861.08; 128/691
[58] Field of Search ........... 73/861.12, 861.15, 861.16, 73/861.08; 128/691

[56] References Cited

U.S. PATENT DOCUMENTS

| 3,967,500 | 7/1976 | Forster | 73/861.06 |
| 4,195,515 | 4/1980 | Smoll | 73/861.13 |
| 4,236,411 | 12/1980 | Ketelsen | 73/861.12 |
| 4,346,605 | 8/1982 | Skladzien et al. | 73/861.13 |
| 4,520,650 | 6/1985 | Palmer et al. | 73/3 |
| 4,635,486 | 1/1987 | Jacobsen et al. | 73/861.12 |
| 4,727,754 | 3/1988 | Ruckel | 73/861.12 |
| 4,881,413 | 11/1989 | Georgi et al. | 73/861.12 |
| 5,090,250 | 2/1992 | Wada | 73/861.12 |
| 5,220,841 | 6/1993 | Brown et al. | 73/861.12 |

FOREIGN PATENT DOCUMENTS

| 0153662 | 12/1979 | Japan | 73/861.15 |
| 901872 | 12/1975 | U.S.S.R. | 73/861.15 |

Primary Examiner—Richard E. Chilcot, Jr.
Assistant Examiner—Elizabeth L. Dougherty
Attorney, Agent, or Firm—Robert E. Bushnell

[57] ABSTRACT

An electromagnetic flow meter for measuring the flow of conductive fluids, e.g. blood, in an extracorporeal circuit. The electromagnetic flow meter utilizes two electromagnets positioned in the housing of a transducer unit, and a disposable insert easily insertable into a tray which slides into a cavity of the housing. The electromagnets generate, at any one time, two magnetic fields having same directions. The conductive fluid flows in a direction perpendicular to the direction of the magnetic fields for inducing first and second voltages. First and second voltage sensing electrodes extend into the bore of the disposable insert and provide the voltages, generated by the fluid flow cutting through the magnetic fields, to first and second slide terminals in the housing. The voltages are provided to a summation amplifier via respective isolation amplifiers, wherein the summation amplifier generates a summation voltage proportional to the flow rate of the conductive fluid passing through the magnetic fields.

13 Claims, 5 Drawing Sheets

BIOPROBE REPLACEMENT SENSOR AND TRANSDUCER

CROSS-REFERENCE TO RELATED APPLICATIONS

This application makes reference to, incorporates the same herein, and claims all benefits incurring under 35 U.S.C. §120 from an application for "A Dual Electromagnet Partially Disposable Fluid Flow Transducer With Side-By-Side Electrodes" filed on 7 Jan. 1994 and assigned Ser. No. 08/178,562.

BACKGROUND OF THE INVENTION

This invention is related to electromagnetic flow meters, and more specifically, relates to a replacement transducer for known transducers used in extracorporeal measurement of blood flow or other conductive liquids.

The use of electromagnetic flow meters to measure fluid flow of conductive fluids, such as blood, is well known. A basic concept, for example, is described in U.S. Pat. No. 2,149,847. By passing blood, either in a tube or blood vessel oriented at right angles to a magnetic field, an electromagnetic field, EMF, is produced at right angles to the magnetic field and at right angles to the direction of blood flow, since the blood has the property of a moving conductor cutting through the magnetic field. The voltage generated is proportional to the velocity of flow and therefore directly proportional to the volume rate of flow of the fluid. The voltage can be measured by electrodes placed at diametrically opposite points of the tube along a diameter extending perpendicular to the magnetic lines of the flux.

Because the electrodes, magnet structure, and fluid passage must be maintained in a fixed predetermined relationship in order to maintain accurate calibration of the flow measurement, it has been the practice heretofore to assemble the tube, electrodes, and magnet structure as a unit and direct flow of blood or other conductive fluids through the tubular section in making measurements. It has been my observation that such unitary structure has several disadvantages in extracorporeal use. First, it is difficult to sterilize effectively after use. Also different size units must be provided to accommodate measurements in different size flow lines. Where measurements are to be taken at more than one point in the extracorporeal circuit, a plurality of separate complete flow meter units are required.

My In Line Electromagnetic How Measurement Transducer described in U.S. Pat. No. 4,195,515 improved on prior art electromagnetic measuring units by making the unit into separable parts that can be readily assembled and disassembled. One part includes a tube with electrode sensors that can be disposed of, or readily and easily changed and sterilized by conventional techniques. The other part included a magnet structure for generating the required magnetic field, and quick disconnect electrical connections for the electrodes of the tube. The magnetic structure can be used with different size tubular units so that measurements can be made at different points in a extracorporeal circuit wherein different size tubular units are positioned at said different points. The magnetic structure is simply moved from one tubular unit to another.

The magnetic structure in my '515 device is comprised of a C-shaped magnetic core, a coil winding on the core and at least three female connection terminals for connection to at least three male terminals formed from the electrodes of the tubular unit.

The Blood How Detection Device described by Donald K. Georgi, et al. in U.S. Pat. No. 4,881,413 (hereafter; Bioprobe) is comprised of a reusable transducer unit having six connectors separately positioned to provide three connectors on each diametrically opposite side of a tubular unit inserted therein. The transducer unit comprises a single "C" shaped magnet for producing a magnetic field through which the blood flows. The tubular unit has six electrodes with three electrodes on diametrically opposite sides of the tube and the bore of the tube is narrower in the central section thereof as compared to the end sections. I have noticed that this arrangement of electrodes results in a cumbersome assembly when connecting the tubular unit to the transducer unit. The six electrodes of the disposable tubular units are in contact with the conductive fluid as the fluid flows through the tube. The increased number of electrodes concomitantly increases the surface area of the electrodes in contact with the flowing fluid, thereby causing decreased stability during the measuring process.

SUMMARY OF THE INVENTION

It is therefore, one object of the present invention to provide an improved apparatus for measuring flow of fluid through an extracorporeal circuit.

It is another object to provide a device exhibiting an enhanced stability in measurements made of fluid flowing through extracorporeal circuits.

It is yet another object to provide a partially disposable device for measuring fluid flow through an extracorporeal circuit.

It is a further object to provide a device easily assembled and disassembled for measuring fluid flow through an extracorporeal circuit, that can be quickly assembled to accommodate different sizes of tubular units.

These and other objects may be attained with an improved electromagnetic measuring unit for making measurements in an extracorporeal circuit. The electromagnetic structure contemplates two "C" shaped electromagnets having parallel ends forming poles on diametrically opposite sides and on opposite ends of the insert and positioned to establish separate magnetic fields, a pair of electrical connections and a pair of ground connections. The tube is disposable and has two field electrodes extending from diametrically opposite sides and opposite ends of the tube for connection to the pair of electrical connections in the electromagnetic structure and a pair of diametrically opposed ground electrodes centrally located along the tube, wherein each of said electrodes is disposed within a same horizontal plane. The windings for each electromagnet are wrapped in the same direction around each respective core of each electromagnet so that at any given time the magnetic field at one electrode is in the same direction to the magnetic field at the other electrode.

The reduced number of electrodes results in an electrode surface area in contact with the conductive fluid ⅓ to ⅔ less than that of the Bioprobe thereby enhancing flow stability and resulting in less zero baseline shift during a measurement process. The electrode arrangement also provides for easier assembly and disassembly between the electromagnetic structure and the tubular unit. Further, the electrodes in separate and opposite magnetic fields results in minimized eddy current loops that occur in the Bioprobe caused by the diametrically opposite electrodes being in the same magnetic field and fluid path. Additionally, the present invention overcomes large switching transients formed as a result of the diametrically opposite electrodes form a pickup loop across the conductive fluid.

BRIEF DESCRIPTION FOR THE DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1:
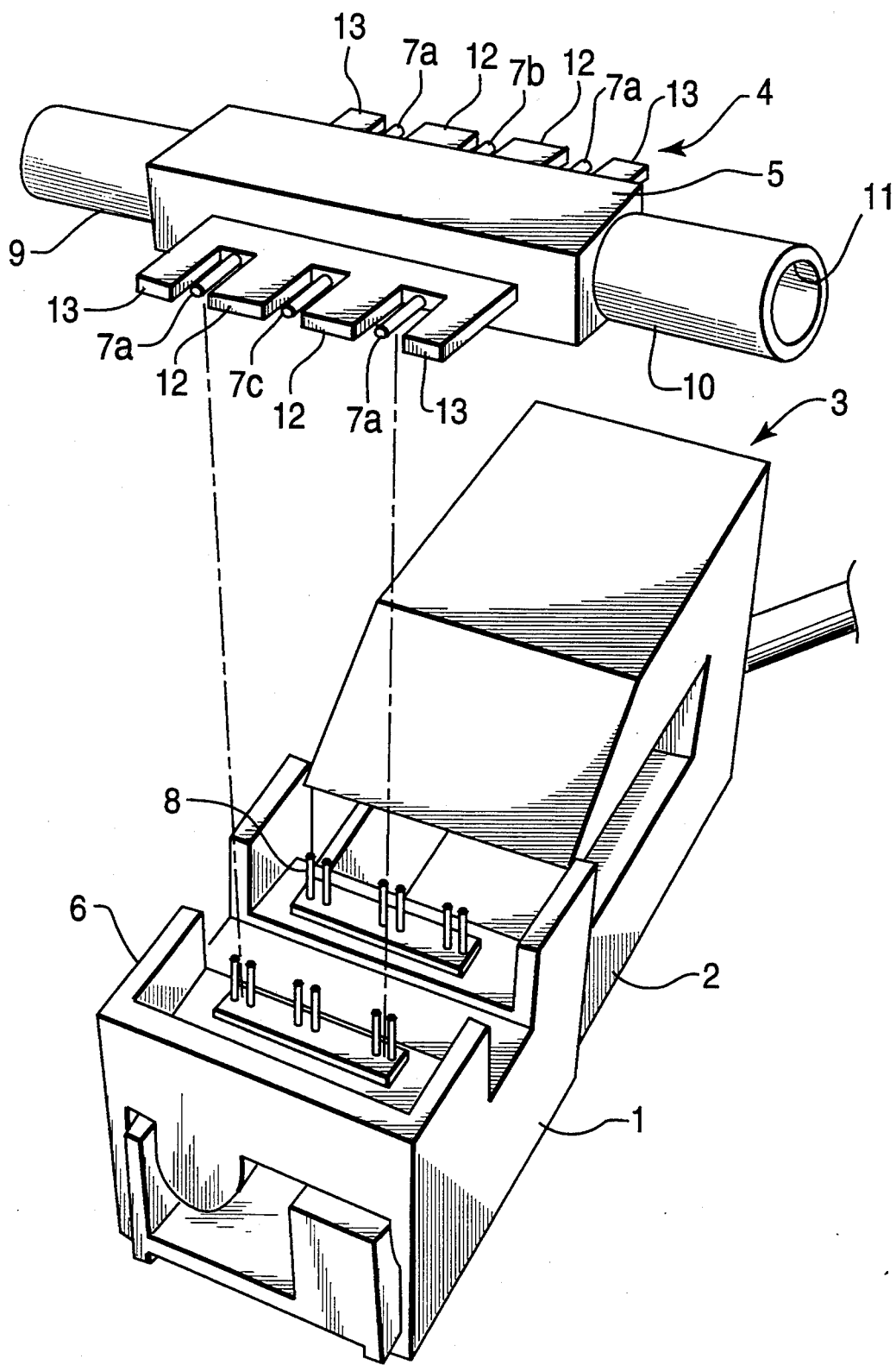
FIG. 1 is a perspective view of a flow tube and transducer in a conventional device.

Referring to the conventional device shown in FIG. 1, a tray assembly 1 is mounted on a slide 2 so that the tray assembly 1 can be moved along the slide 2 to engage a transducer 3. A flow tube (hereafter; sensor) 4 has fins 13 adapted to engage retainer walls 6 of tray 1. Sensor 4 is adapted to be inserted into tray 1 so that the male terminals 7 engage slide terminals 8 on tray 1.

The sensor 4 has tube ends 9 and 10 extending from either end of a body portion 5 for connecting the sensor in the path of a conductive fluid. The male terminals 7 are electrical terminals which extend in pairs from diametrically opposite sides of the body portion 5. Fins 12 and 13 are provided along opposite sides of body portion 5 to provide electrical isolation between the electrical terminals 7 and for assisting in the mounting and stationary positioning of sensor 4 onto tray 1.

In the forgoing description, the male terminals are all generally referred to by reference to male terminals 7. However, since the male terminals are grouped in pairs and each pair has a different electrical function the pairs of electrical male terminals are differentiated by reference to terminals 7a, 7b and 7c. Terminals 7a form an electrical ground for the electrical system and terminals 7b and 7c are designed to pick up or sense the induced voltage generated by the conductive fluid flowing through the duct 11 of sensor 4, and thus through an electromagnetic field as will be discussed further with regard to FIG. 2. A more detailed description of the conventional device shown in FIG. 1 is provided in U.S. Pat. No. 4,881,413, and is incorporated herein by reference.

Figure 2:
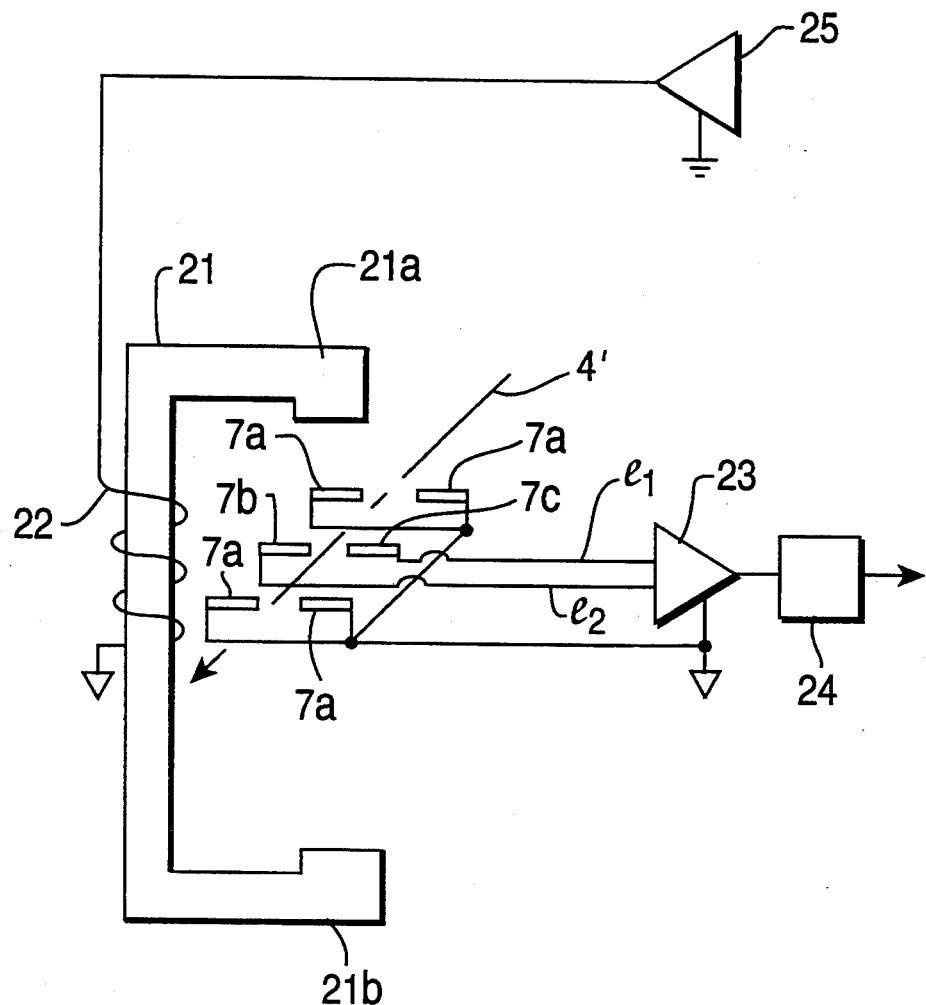
FIG. 2 is an abstract schematic illustration of electrical connections and the relative positioning of an electromagnet and a flow tube of a conventional device.

With regard to FIG. 2, there is shown a representative of an electromagnet 21 having a blocked "C" shape and housed in transducer 3, wherein the electromagnet 21 has a coil 22 which is driven by an AC source 25 for inducing an electromagnetic field in the core of the electromagnet 21. Broken arrow 4' represents sensor 4 and the direction in which the conductive fluid flows through the duct 11 thereof. Electrodes 7b and 7c are placed on diametrically opposite sides of sensor 4 and extend perpendicular to the magnetic lines of the flux (not shown) between each pole 21a and 21b of electromagnet 21. Electrodes 7b and 7c respectively output separate voltages $e_2$ and $e_1$ to an amplifier 23 having a ground reference connected to each of terminals 7a. The generated voltages $e_1$ and $e_2$ are proportional to the velocity of flow and therefore directly proportional to the volume rate of flow of the conductive fluid. The amplified voltage output by amplifier 23 is provided to an isolation transformer 24 which prevents dangerous currents from being circulated in the system.

Note that the sensor 4 does not have a constant circular bore, and actually the duct 11 (FIG. 1) is circular at each end of tube ends 9 and 10 but narrows to a rectangular shape in the area adjacent to electrodes 7b and 7c. thereby resulting in an increased velocity of the fluid flowing through the magnetic lines of flux and resulting in an increase in the induced voltage generated. This increase in induced voltage does not provide a true measurement of the flow rate of the fluid prior to the fluid flowing into the sensor 4, but instead must be analyzed by the operator to determine actual flow rate of the fluid prior to the fluid flowing into the sensor 4, which may result in operator error.

Figure 3:
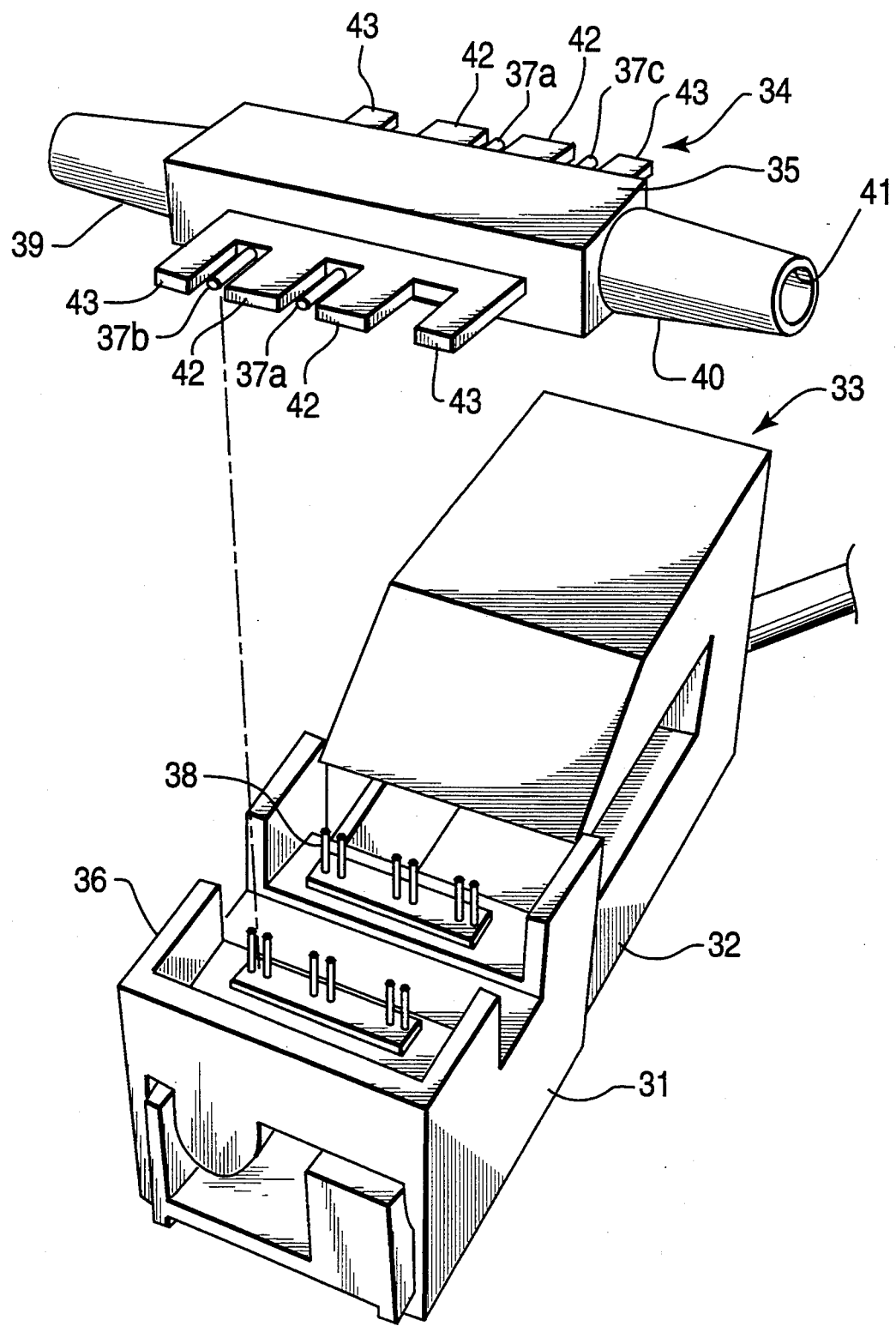
FIG. 3 is a diagrammatic view of a flow tube and transducer of the present invention.

FIG. 3 illustrates the present invention wherein a tray assembly 31 is mounted on a slide 32 so that the tray assembly 31 can be moved along the slide 32 to engage a transducer 33. A flow tube (hereafter; sensor) 34 has fins 43 adapted to engage retainer walls 36 of tray 31. Sensor 34 is adapted to be inserted into tray 31 so that the male terminals 37 engage slide terminals 38 on tray 31.

The sensor 34 has tapered tube ends 39 and 40 extending from either end of a body portion 35 for connecting the sensor in the path of a conductive fluid. The male terminals 37 are electrical terminals which extend from diametrically opposite sides of the body portion 35. Fins 42 and 43 are provided along opposite sides of body portion 35 to provide electrical isolation between the electrical terminals 37 and for assisting in the mounting and stationary positioning of sensor 34 onto tray 31.

In the forgoing description, the male terminals are all generally referred to by reference to male terminals 37. However, since each male terminal has a different electrical function the electrical male terminals are differentiated by reference to terminals 37a, 37b and 37c. Terminals 37a form an electrical ground for the electrical system and terminals 37b and 37c are designed to pick up or sense the induced voltages generated by the conductive fluid flowing through duct 41 of sensor 34, and thus through separate electromagnetic fields as will be discussed further with regard to FIG. 4.

Figure 4:
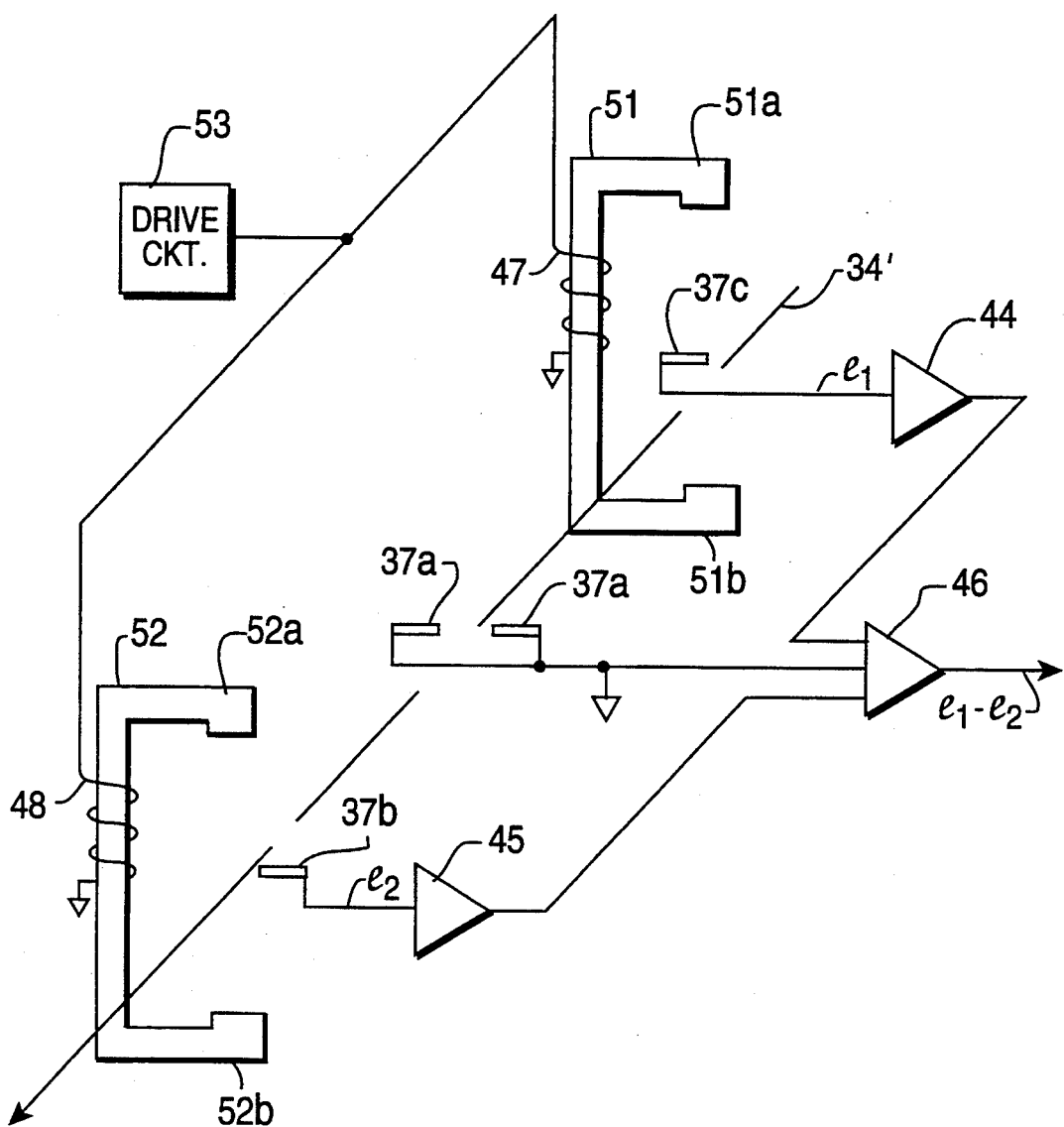
FIG. 4 is an abstract schematic illustration of the electrical connections according to the relative positioning of the electromagnets and the flow tube of the present invention.
Figure 5:
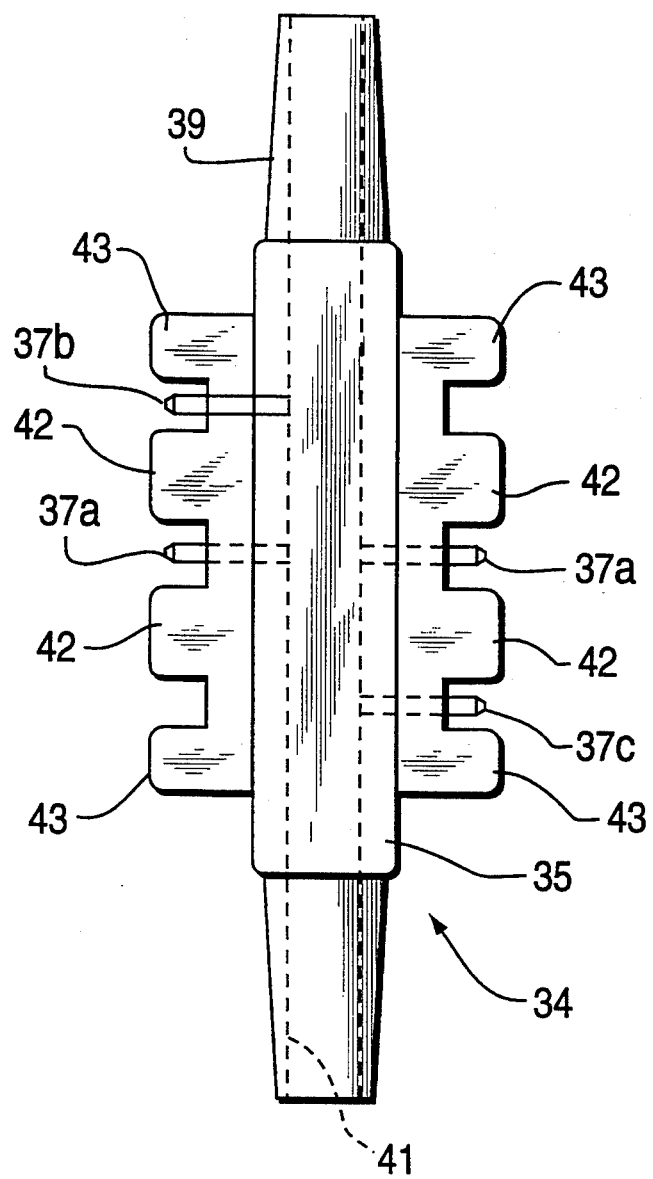
FIG. 5 is an overhead view illustrating the relationship of the bore in the flow tube of the present invention.

With regard to FIG. 5, the sensor 34 of the inventive device differs from the sensor 4 of the conventional device shown in FIG. 1 in that the duct 41 has a constant diameter so that the flow rate of the conductive fluid is not unnecessarily altered. Also, the tube ends are tapered so as to fit more easily into the conductive fluid carrier, i.e. blood vessel, hose, etc., the conductive fluid path. Additionally, electrodes 37a provide a ground reference in the central area of the sensor 34, whereas an induced voltage was generated in the central area of the conventional device. Further, electrodes 37b and 37c are still on opposite sides of the sensor 34 but are disposed on separate ends of sensor 34 instead of being directly opposite each other, and each respectively measures the induced voltage generated in response to the conductive fluid passing through two separate magnetic fields as will be discussed further with regard to FIG. 4. Additionally, sensor 34 is disposable and may be made in different sizes such that a sensor having a bore size proportional to the size of the conductive fluid carrier may be properly provided.

It is noted that tray 31 may be the same as tray 1 of the conventional device, but the leads from slide terminal 38 are connected in a different manner to further components than the leads from the slide terminals 8 of the conventional device as described below with respect to FIG. 4.

FIG. 4 depicts two electromagnets 51 and 52 each having a blocked "C" shape and being housed in transducer 33 to be disposed over electrodes 37c and 37b, respectively. Each electromagnet 51 and 52 is wrapped with a coil 47 and 48, respectively, wherein each coil is wrapped in the same direction around their respective electromagnet. Further, each coil is commonly driven by a drive circuit 53 for inducing separate electromagnetic fields in each core of electromagnets 51 and 52. Broken arrow 34' represents sensor 34 and the direction in which the conductive fluid flows through the duct 41 thereof. Each electrode 37c and 37b is placed on diametrically opposite sides and on opposite ends of sensor 34, and extend perpendicular to the magnetic lines of the flux (not shown) respectively between poles 51a and 51b of electromagnet 51 and poles 52a and 52b of electromagnet 52. Electrodes 37c and 37b respectively output a separate voltage $e_1$ and $e_2$ (via slide terminals 38). Isolation amplifiers, or buffers, 44 and 45 are provided to respectively isolate voltages $e_1$ and $e_2$ from further circuits to prevent dangerous currents from being feedback to the electrodes and from being circulated in the system. Summation amplifier 46 has a ground reference connected to each of electrodes 37a and is further connected to the outputs of the isolation amplifiers 44 and 45 to receive the voltages $e_1$ and $e_2$ and output a summation voltage $e_1+e_2$. The generated summation voltage $e_1+e_2$ is proportional to the velocity of flow and therefore directly proportional to the volume rate of flow of the conductive fluid.

Having specifically described a preferred embodiment of the invention, it will be apparent that the invention is not limited to such embodiment, and that modifications and variations, e.g. sensor 34 may be made without electrodes 37a, may be effected therein by one skilled in the art without departing from the spirit or scope of the present invention as defined in the appended claims.

A further embodiment may be comprised of the transducer unit housing a pair of "C" shaped electromagnets having parallel ends forming the poles on diametrically opposite sides if the insert, the cores of the electromagnets being wrapped in opposite directions by a single winding, wherein the insert may comprises two electrodes extending from the same side of the electrodes and perpendicular to the electromagnetic fields generated by the electromagnets.

What is claimed is:

1. An electromagnetic flow meter for measuring a flow rate of a conductive fluid, comprising:

transducer means having a blocked "C" shaped housing, said transducer means comprising a first electromagnet with a first winding wrapped around said first electromagnet in a first direction, a second electromagnet with a second winding wrapped around said second electromagnet in said first direction, said first and second windings receiving a driving signal from a common drive source;

tray means having a plurality of slide terminals, said tray means being slidably insertable into a cavity of said transducer means;

insert means for insertion into an extracorporeal circuit comprising a rectangular central section having a constant tubular bore, said central section being insertable into said tray means, said central section comprising a first voltage sensing electrode, a second voltage sensing electrode and a pair of diametrically opposing ground electrodes extending into said tubular bore of said central section for contacting said conductive fluid, said first voltage sensing electrode and said second voltage sensing electrode being separated from each other by said ground electrodes and being disposed on opposite sides of said central section along a same diametrical plane, said first and second voltage sensing electrodes and said ground electrodes extending radially outward from said central section for insertion into respective ones of said plurality of slide terminals;

said insert means having first and second end portions each having a conical shape for enabling said insert means to be inserted into said extracorporeal circuit, said first and second end portions each having a constant tubular bore diametrically equal to the constant tubular bore of said central section for enabling said blood to flow unimpaired through said insert means.

2. The electromagnetic flow meter as set forth in claim 1, each of said first and second electromagnets having a first pole and a second pole wherein said first pole is positioned over said cavity of said transducer means and said second pole is positioned below said cavity, said first and second electromagnets generate respective magnetic fields having directions of flow perpendicular to the flow of said conductive fluid flowing through the tubular bore of said insert means in response to said driving signal.

3. The electromagnetic flow meter as set forth in claim 2, said first electrode for picking up a first induced voltage in response to said conductive fluid flowing through and perpendicular to said magnetic field produced by said first electromagnet.

4. The electromagnetic flow meter as set forth in claim 2, said second electrode for picking up a second induced voltage in response to said conductive fluid flowing through and perpendicular to said magnetic field produced by said second electromagnet.

5. The electromagnetic flow meter as set forth in claim 2, said first electrode for picking up a first induced voltage in response to said conductive fluid flowing through and perpendicular to said magnetic field produced by said first electromagnet, and said second electrode for picking up a second induced voltage in response to said conductive fluid flowing through and perpendicular to said magnetic field produced by said second electromagnet.

6. The electromagnetic flow meter as set forth in claim 5, further comprising:

an amplifier for generating a summation voltage in response to reception of said first and second induced voltages;

a first isolation means connected between said first electrode and said amplifier; and a second isolation means connected between said second electrode and said amplifier;

said first and second isolation means preventing feedback of undesired currents from said amplifier to said extracorporeal circuit.

7. The electromagnetic flow meter as set forth in claim 6, further comprising a grounding reference connected to said ground electrodes and to said amplifier.

8. An electromagnetic flow meter for measuring a flow rate of a conductive fluid and having transducer means having a blocked "C" shaped housing for housing a first electromagnet with a first winding wrapped around said first electromagnet in a first direction, and a second electromagnet with a second winding wrapped around said second electromagnet in said first direction, said first and second windings receiving a driving signal from a common drive source, and tray means having a plurality of slide terminals, said tray means being slidably insertable into a cavity of said transducer means, said electromagnetic flow meter comprising:

sensor means for insertion into an extracorporeal circuit, said sensor means comprising:

a central section having a constant tubular bore and being insertable into said tray means, said central section comprising a first voltage sensing electrode and a second voltage sensing electrode extending into said tubular bore of said central section for contacting said conductive fluid, said first voltage sensing electrode and said second voltage sensing electrode being disposed on opposite ends and on opposite sides of said central section along a same diametrical plane, said first and second voltage sensing electrodes extending radially outward from said central section for insertion into respective ones of said plurality of slide terminals;

a pair of diametrically opposing ground electrodes extending into said tubular bore of said central section for contacting said conductive fluid, said ground electrodes extending radially outward from said central section, centrally positioned between said first and second electrodes and in the same diametric plane as said first and second electrodes for insertion into respective ones of said plurality of slide terminals; and first and second end sections each having a conical shape for enabling said sensor means to be inserted into said extracorporeal circuit, said first and second end portions each having a constant tubular bore diametrically equal to the constant tubular bore of said central section for enabling said conductive fluid to flow unimpaired through said insert means.

9. An electromagnetic flow meter as claimed in claim 8, said sensor means further comprising:

a plurality of fins provided along diametrically opposite sides of central section and in the same diametric plane as said first and second voltage sensing electrodes and said ground electrodes, said fins providing electrical isolation between said first and second voltage sensing electrodes and said ground electrodes, said fins assisting in fixedly positioning said sensor means into said tray means.

10. An electromagnetic flow meter as claimed in claim 8, further comprising said first voltage sensing electrode for picking up a first induced voltage in response to said conductive fluid flowing through and perpendicular to a first magnetic field generated by said first electromagnet, and said second voltage sensing electrode for picking up a second induced voltage in response to said conductive fluid flowing through and perpendicular to a second magnetic field generated by said second electromagnet.

11. An electromagnetic flow meter as claimed in claim 8, wherein said sensor means is disposable.

12. An electromagnetic flow meter sensing insert comprising:

a central section having a constant tubular bore, said central section comprising a first voltage sensing electrode and a second voltage sensing electrode extending into said tubular bore of said central section for contacting conductive fluid in an extracorporeal circuit for sensing a first induced voltage and a second induced voltage, respectively, said first voltage sensing electrode and said second voltage sensing electrode being disposed on opposite ends and on opposite sides of said central section along a same diametrical plane, said first and second voltage sensing electrodes extending radially outward from said central section; and first and second end sections each having a conical shape for enabling said sensor means to be inserted into said extracorporeal circuit, said first and second end portions each having a constant tubular bore diametrically equal to the constant tubular bore of said central section for enabling said conductive fluid to flow unimpaired through said insert means.

13. An electromagnetic flow meter sensing insert as claimed in claim 12, further comprising:

a pair of diametrically opposing ground electrodes extending into said tubular bore of said central section for contacting said conductive fluid, said ground electrodes extending radially outward from said central section, centrally positioned between said first and second electrodes and in the same diametric plane as said first and second electrodes.

* * * * *